United States Patent
Shirzad et al.

(10) Patent No.: US 6,698,288 B2
(45) Date of Patent: Mar. 2, 2004

(54) METHOD AND SYSTEM FOR ASSEMBLING AND NONDESTRUCTIVE TESTING OF ASSEMBLIES WITH COMPOSITE COMPONENTS

(75) Inventors: Shahram Shirzad, Castskill, NY (US); John Ruediger Mader Viertl, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 92 days.

(21) Appl. No.: 10/010,127

(22) Filed: Dec. 6, 2001

(65) Prior Publication Data

US 2003/0106376 A1 Jun. 12, 2003

(51) Int. Cl.[7] .............................. G01N 29/04; G01J 5/02
(52) U.S. Cl. ........................ 73/577; 250/341.6; 250/334
(58) Field of Search .......................... 73/606, 607, 615, 73/1.82, 629; 250/341.6, 334

(56) References Cited

U.S. PATENT DOCUMENTS

| | | | | |
|---|---|---|---|---|
| 4,550,255 A | * | 10/1985 | Sve et al. | 250/359.1 |
| 4,806,292 A | * | 2/1989 | DeLacy | 264/40.1 |
| 5,616,865 A | * | 4/1997 | Webster | 73/627 |
| 6,236,049 B1 | * | 5/2001 | Thomas et al. | 250/341.6 |
| 6,399,948 B1 | * | 6/2002 | Thomas et al. | 250/341.6 |
| 6,532,819 B1 | * | 3/2003 | Chen et al. | 73/606 |
| 6,543,287 B1 | * | 4/2003 | Davis | 73/606 |

OTHER PUBLICATIONS

Photonics Tech Briefs, Finding cracks and checking out walnuts, Mar. 2000.*
ThermoSonix, A Novel Infrared and Ultrasonic–Based System fro non–destructive testing built with Labview, IMAQ Vision and DAQ., Mar. 2000.*
Lockin Thermography methods for the NDT of CFRP aircraft components, Jun. 2002.*
L. D. Favro et al. in "Infrared Imaging of Defects Heated by a Sonic Pulse," Review of Scientific Instruments, vol. 71, No. 6 (Jun. 2000), p. 2418–2421.

* cited by examiner

Primary Examiner—Hezron Williams
Assistant Examiner—Jacques Saint-Surin
(74) Attorney, Agent, or Firm—Ernest Cusick; Gary M. Hartman; Domenica N.S. Hartman

(57) ABSTRACT

A method and system for nondestructively detecting and characterizing defects in articles, including assemblies that may include components formed of composite materials. The method entails vibrating an entire article/assembly to induce an oscillating strain in the article/assembly so that any flaws in the article/assembly are heated by localized friction, as would occur between opposing surface portions of a defect or an interface between components of the assembly. The article/assembly is then infrared imaged to detect any localized temperature rises associated with the localized friction at the defect or interface.

32 Claims, 2 Drawing Sheets

METHOD AND SYSTEM FOR ASSEMBLING AND NONDESTRUCTIVE TESTING OF ASSEMBLIES WITH COMPOSITE COMPONENTS

CROSS REFERENCE TO RELATED APPLICATIONS

Not applicable.

STATEMENT REGARDING FEDERALLY SPONSORED RESEARCH

Not applicable.

BACKGROUND OF THE INVENTION (1) Field of the Invention

The present invention generally relates to the manufacturing and testing of composite articles. More particularly, this invention relates to a method and system for assembling and nondestructively detecting and characterizing flaws in an assembly that includes a composite component.

(2) Description of the Related Art

Higher operating temperatures for gas turbine engines are continuously sought in order to increase their efficiency. However, as operating temperatures increase, the high temperature durability of the components of the engine must correspondingly increase. Significant advances in high temperature capabilities have been achieved through the formulation of iron, nickel and cobalt-base superalloys. Yet as higher temperatures are required for gas turbine engines, alternative materials have been proposed. Materials containing silicon, particularly ceramic matrix composite (CMC) materials with silicon carbide (SiC) as a matrix material and/or as a reinforcing material, are currently being considered for high temperature applications, such as combustor and other hot section components of gas turbine engines.

In the effort to develop CMC composites for gas turbine engine applications, there is a need to be able to assemble composite components with other structures, and nondestructively detect and characterize any processing or operational flaws below the component surface as well as any assembly flaws. Due to their composite nature and the relatively low atomic numbers of the elements from which CMC's are formed, traditional nondestructive methods such as ultrasonic and x-ray testing are not fully satisfactory. Though ultrasonic testing has been used to detect and characterize flaws in composite materials, it cannot be easily used to distinguish between small flaws in a CMC component and fluctuations due to modulus and density variations that are inherent in CMC components. While effective for detecting and evaluating volumetric flaws in CMC composites, x-ray detection methods have not been very effective when used on low atomic number materials. Furthermore, x-ray detection methods have not been effective in detecting delaminations, which are a relatively common type of flaw in CMC components.

While infrared (IR) detection methods have been successfully used to detect and estimate the depth of delaminations in composites, local thermal conductivity variations in CMC composite materials can mimic local delaminations in certain situations. In addition, the ability of IR detection methods to estimate flaw depth is limited by the thermal radiation of the surrounding material, which can result in a situation in which a small signal must be detected in a large and "noisy" thermal background. At some levels of sensitivity, it becomes difficult to distinguish between a small flaw and ordinary variations in a composite material. Recent work reported by L. D. Favro et al. in "Infrared Imaging of Defects Heated by a Sonic Pulse," Review of Scientific Instruments, Vol. 71, No. 6 (June 2000), involves using IR imaging to detect localized frictional heating generated at subsurface defects by sonic excitation. However, Favro et al. describe using short pulses (50 to 200 ms) of high frequency (e.g., 20 to 40 kHz) applied to limited points on the surface of the object being inspected, which can be impractical or cumbersome when the object to be examined is large and/or an assembly of components whose various interfaces can be the location for flaws.

In view of the above, it would be desirable if an improved method were available for nondestructively detecting and characterizing flaws in a composite article, such as CMC articles, particularly with respect to detecting assembly defects and delaminations within such articles.

BRIEF SUMMARY OF THE INVENTION

The present invention provides a method and system for nondestructively detecting and characterizing defects in articles, and particular assemblies that may include a component formed of a composite material. The method generally entails vibrating an entire article to induce an oscillating strain in the article so that any flaws in the article are heated by localized friction, as would occur between opposing surface portions of a defect or an interface between components of an assembly. The oscillating strain can be induced with a variety of known methods, such as using a piezoelectric element or another suitable device. The article is then infrared imaged to detect any localized temperature rises in the article associated with the localized friction at a defect.

From the above, one can appreciate that the method and system of this invention are able to detect and characterize flaws nondestructively in composite materials and assemblies comprising a composite article. A particular advantage of the invention is that thermal signatures generated from tight flaws are quite large compared to the thermal background of a composite article being examined, thereby significantly improving the capability of detecting even relatively small flaws and defects. These enhanced flaw signatures are conducted to the surface of the article, where they can be detected by infrared imaging device.

Another feature of the method and system of this invention is the ability to detect inadequate clamping loads generated by fasteners that secure components of an assembly together, which when subject to the oscillating strain causes frictional heating at the interfaces between the mating surfaces of the components. By detecting fasteners with low clamping loads, such fasteners can be tightened or replaced as necessary, and/or the installation of fasteners of subsequently produced assemblies can be modified to achieve adequate clamping loads. If one of the components is formed of a composite material, another benefit of the invention is that the vibrating step causes projecting features typically present on the surfaces of composite component to be reduced by wear or grinding. As such, the method can be employed to improve the interface of a composite component with a second component of the assembly, after which the fasteners that hold the components together can be tightened or replaced as necessary. While particularly well suited for use on composite materials and assemblies comprising composite articles, the test method and system of this invention could be adapted for use with other materials and assemblies, such as to detect welding flaws in metals.

DETAILED DESCRIPTION OF THE INVENTION

Figure 1:
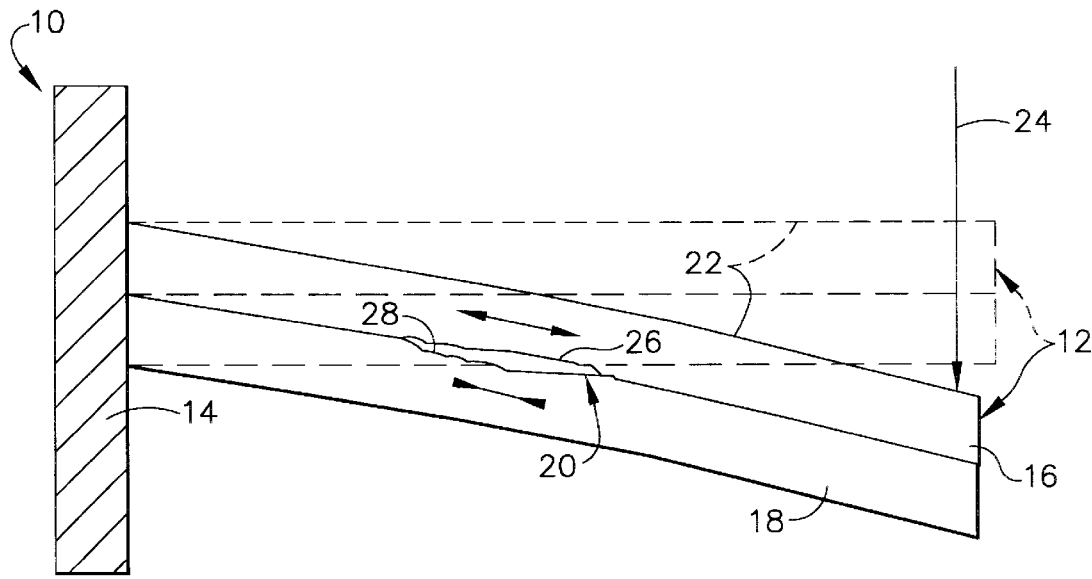
FIG. 1 is a schematic representation showing an oscillating strain induced in an article fixtured as a cantilever for the purpose of nondestructively detecting a flaw in the article in accordance with a first embodiment of this invention.
Figure 4:
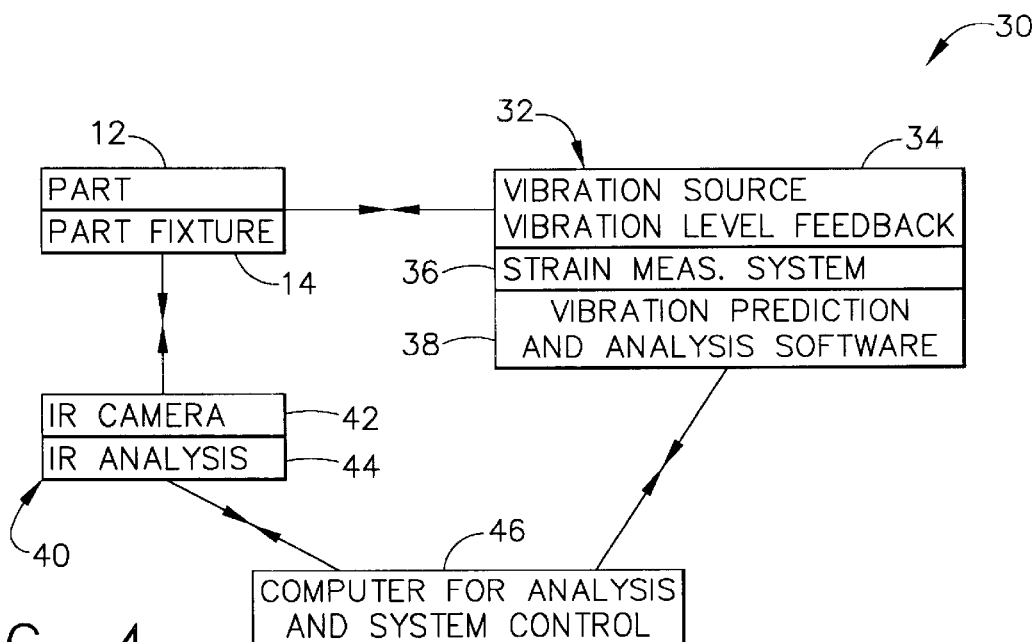
FIG. 4 is a schematic representation of a thermo-vibration system for carrying out the procedures represented in FIGS. 1, 2 and 3.

FIGS. 1 and 4 schematically represent a test apparatus and system for nondestructively detecting and characterizing flaws within components formed of composite materials and assemblies containing such components. The apparatus and system make use of a combination of high level oscillating strains to produce frictional heating of opposing surface portions of a flaw or defect, and detection of the generated frictional heat that is conducted to the surface of the article. While the invention has been found to be particularly useful for analyzing components and assemblies containing laminated composite materials, such as of the type used to form components for gas turbine engines, the invention is applicable to laminated, particle and fiber-reinforced composite materials intended for a wide variety of applications.

In FIG. 1, an apparatus 10 is represented with an article 12 mounted or supported from a fixture 14 using any suitable means, such that the article 12 is cantilevered from the fixture 14. The article 12 is schematically represented as being a laminated composite material, comprising laminations 16 and 18 and having a panel-like symmetrical shape, though a variety of other materials, constructions and shapes could have been represented. The article 12 is also represented as containing a flaw 20 in the form of a delamination between the laminations 16 and 18, and therefore lying in a plane parallel to the upper surface 22 of the article 12, though flaws oriented in a plane normal to the surface 22 are also possible in laminated composites of the type represented in FIG. 1. Finally, the article 12 is shown as being deflected downward in response to an oscillating force 24 coupled to the distal end of the cantilevered article 12. According to the invention, the oscillation force 24 is at a sufficient level to induce an oscillating strain effectively throughout the entire article 12, and the oscillating strain causes localized friction between opposing surface portions 26 and 28 of the flaw 20 as these surface portions 26 and 28 contact and move relative to each other. This friction causes localized heating of the article 12 in the immediate vicinity of the flaw 20.

Importantly, the localized heating made possible with this invention produces a thermal signature that can be distinguished from the thermal background noise resulting from ordinary material and physical variations present in a composite material. For example, smaller flaws can be detected with the present invention than otherwise possible with prior art methods using infrared detection or other known heat detection devices. In practice, the method of this invention has employed infrared detection to successfully detect and estimate the depth of delaminations in CMC articles, even where local thermal conductivity variations in the CMC material mimics local delaminations when examined using infrared methods.

The article 12 is preferably secured to the fixture 14 at a convenient set of nodal points of the article 12, and the oscillating force is applied at an anti-nodal point of the article 12. Suitable vibration frequencies are generally in the range of about 0.01 to about 250 kHz, more preferably in the range of about 20 to about 40 kHz, depending on the physical characteristics (including natural frequency) of the article 12. Various means are known and capable of applying the oscillating force 24, such as a piezoelectric element, or a tensile or high cycle fatigue machine. For example, mechanical vibrations can be induced with a piezoelectric element by an oscillating voltage. An exponential horn (amplitude multiplier) can be attached to the piezoelectric element to enhance the vibration amplitude applied to the article 12.

An important aspect of this invention is the ability to create an oscillating strain gradient across essentially the entire article 12, such that the resulting localized friction and heating between the surfaces of any flaws or defects within the article 12 can be detected by examining the exterior of the article 12 for localized elevated temperatures. FIG. 4 represents a thermo-vibration system 30 for inducing and controlling the oscillating force 24 represented in FIG. 1, as well as equipment for detecting temperature rises in the article 12. For the purpose of inducing the oscillating strain gradient in the article 12, FIG. 4 represents a vibration system 32 that includes a vibration source 34, including vibration level feedback (e.g., an accelerometer) for detecting the frequency and amplitude of the vibration induced in the article 12 by the oscillating force 24. The vibration system 32 further includes a strain measuring system 36, which may be a strain gage attached to the article 12, and a vibration prediction and analysis system 38 by which the vibration induced in the article 12 can be controlled through use of feedback from the strain measuring system 36. Equipment suitable for each of these systems is well known to those skilled in the art, and therefore will not be described here in any detail.

An infrared detection system 40 is represented in FIG. 4 for detecting localized temperature rises in the article 12. The infrared detection system 40 includes an infrared camera 42 and analyzer 44, which together produce an infrared image of the article 12 that can then be analyzed for temperature differences present at the surfaces of the article 12. In most cases, it will be desirable for the infrared detection system 40 to be capable of displaying a visual image by which locally heated regions of the article 12 can be seen by an observer. Both the vibration system 32 and the infrared detection system 40 are shown as communicating with a computer 46 for controlling the thermo-vibration system 30 as well as analyzing the thermal data obtained from the infrared detection system 40.

In practicing the present invention for the purpose of nondestructive analysis, the preference is to apply high levels of mechanical strain to maximize frictional heating, but within the elastic region of the stress-strain curve of the particular material so as to avoid permanent damage to the article caused by plastic deformation. Accordingly, the elastic strain region should first be determined for any article that is to be analyzed by the method of this invention. For a number of ceramic composite materials, the elastic strain region is below 0.05% strain. Various methods and equipment are known for ascertaining the stress-strain characteristics of a composite material, and will not be discussed here in any detail.

The method of this invention is selective for particular flaw orientations based upon the orientation of the applied strains to the article 12. For CMC articles, a typical flaw is due to delamination of the internal layers, as depicted in FIG. 1. A delamination flaw of the type represented in FIG. 1 is typically in the plane of the article 12 or perpendicular to the plane of the article 12. Frictional heating of a delamination flaw is most effectively induced by applying an oscillating shearing strain across the delamination surfaces. As represented in FIG. 1, for flaws in the plane of the article 12 (i.e., parallel to a major surface 22 of the article 12), excitation perpendicular to the plane of reference is effective. On the other hand, excitation parallel to the major plane of an article is effective to excite transverse cracks and other flaws oriented perpendicular to the plane of reference.

Figure 2:
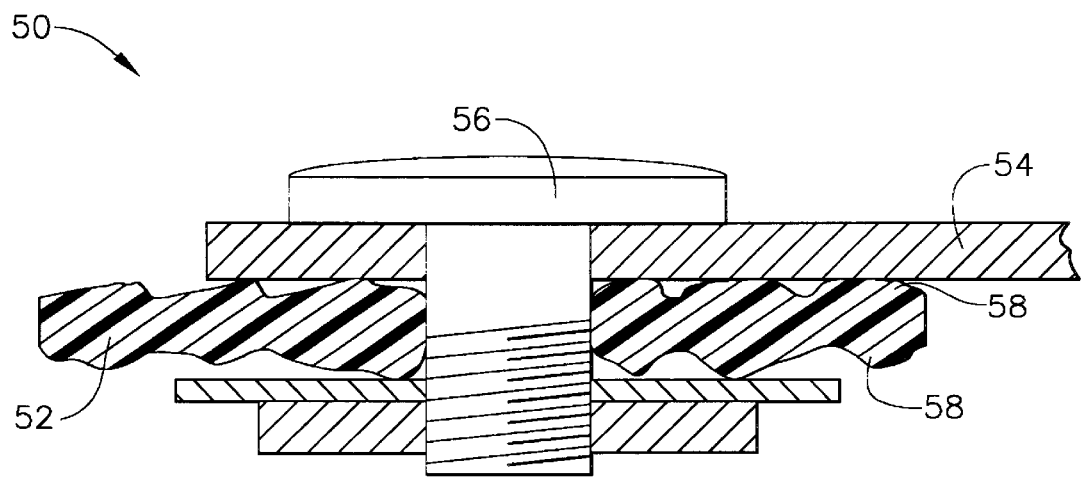
FIG. 2 depicts an assembly that includes a composite component, and represents the appearance of the assembly prior to carrying out a procedure in accordance with a second embodiment of this invention.
Figure 3:
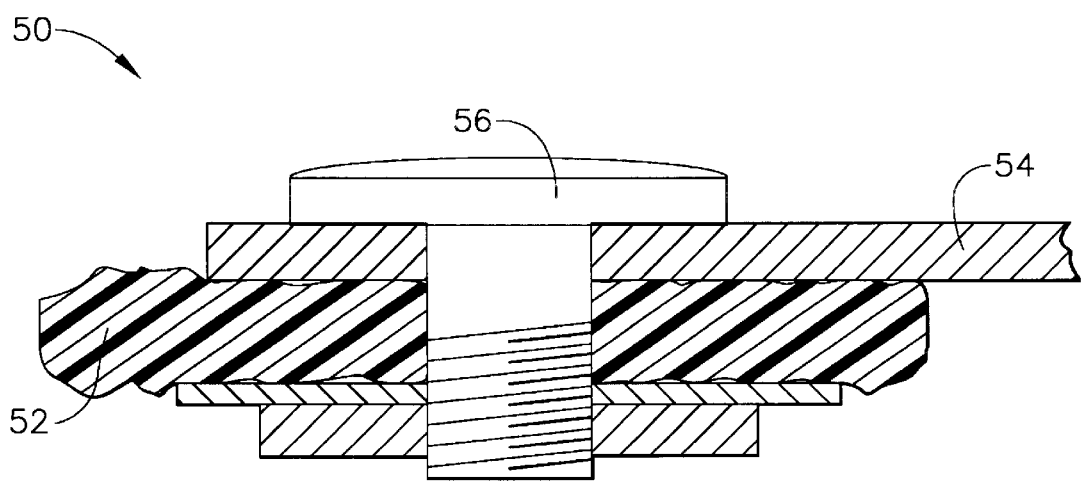
FIG. 3 depicts the assembly of FIG. 2 after carrying out the procedure in accordance with the second embodiment of this invention.

In FIGS. 2 and 3, an assembly 50 is represented as comprising a composite component 52 secured to a second component 54 with a fastener 56, such as the threaded nut and bolt assembly represented in FIGS. 2 and 3, though other fasteners (e.g., rivets) could be used. The second component 54 may be a support structure formed of metal to which the composite component 52 is mounted, though it is foreseeable that the second component 54 could also be formed of other materials, including a composite material. The composite component 52 is schematically represented as being hard and having an irregular surface with raised or projecting surface features 58. As such, the interface between the components 52 and 54 is not tight. As assembled, considerable variability may occur in the clamping load generated by any given rivet of the assembly 50 as a result of the surface features 58, including their size and mechanical properties (e.g., hardness and strength) that affect the ability of the features 58 to resist compaction, collapse and wear. During service, these features 58 can break down and wear, considerably reducing the clamping load of the fastener 56. As such, the features 58 and the gaps therebetween can be viewed as a source of flaws or defects at the interface between the components 52 and 54.

A problem with assemblies of the type shown in FIGS. 2 and 3 is the difficulty with which appropriate fastener loads are obtained that will prevent the components 52 and 54 from moving or sliding relative to each other. According to the invention, the system 30 of FIG. 4 can be used to observe the frictional heat generated between the components 52 and 54 when subjected vibration that induces an oscillation strain in the assembly 50. For this purpose, the assembly 50 is preferably secured to a fixture as described in reference to the apparatus 10 of FIG. 1, e.g., at a convenient set of nodal points of the assembly 10, and the oscillating force is applied at an anti-nodal point of the assembly 50. Again, suitable vibration frequencies will depend on the physical characteristics (including natural frequencies) of the assembly 50, though frequencies generally in the range of about 0.01 to about 100 kHz will typically be acceptable. The fastener 56 applies a clamping force between the components 52 and 54 that produces a frictional force between their mating surfaces, such that the components 52 and 54 will not move relative to each other unless vibrated at a level that generates forces that exceed the frictional force. As such, under appropriate vibration conditions, the surfaces of the components 52 and 54 will move relative to each other, generating heat that can be detected with the system 30 shown in FIG. 4. In this manner, a fastener 56 that does not provide an adequate clamping load can be identified by IR imaging and then tightened, repaired or replaced as the case may be.

The thermo-vibrational analysis capability of this invention can also be used to provide an additional benefit to the production of assemblies of the type represented in FIGS. 2 and 3, by wearing or otherwise reducing the surface features 58 of the composite component 52, followed by tightening, repairing or replacing the fastener 56 as represented in FIG. 3. Accordingly, the invention can also be part of an assembly process, in which mechanical vibration and IR imaging are used to improve the interface between the composite component 52 (which will typically be hard and relatively brittle if formed of a CMC material) and the second component 54, as well as monitor the integrity of the assembly 50 by detecting the level of frictional heating between the components 52 and 54. Low levels of heating will indicate an acceptable joint loading stress. Furthermore, adequate and reliable clamping loads can be achieved by tightening, repairing or replacing fasteners based on the results of the thermally monitored vibration process of this invention, while avoiding the crushing of surface features 58 and breakage of the composite component 52 during assembly.

While the invention has been described in terms of a preferred embodiment, it is apparent that other forms could be adopted by one skilled in the art. For example, various methods and equipment could be used to create an oscillation strain that is sufficient to cause frictional heating of flaws within an article, and various methods and equipment could be used to detect temperature increases attributable to such frictional heating. Therefore, the scope of the invention is to be limited only by the following claims.

What is claimed is:

1. A method of nondestructively detecting defects in an article, the method comprising the steps of:
   fixturing the article so as to be secured at at least one nodal point of the article;
   vibrating the entire article by applying an oscillating force at an anti-nodal point of the article to induce an oscillating strain in the article; and then
   infrared imaging the article to detect a temperature rise in the article associated with friction caused by the oscillating strain and localized at a defect in the article.

2. A method according to claim 1, wherein the oscillating strain is within the elastic strain region of the article.

3. A method according to claim 1, wherein the oscillating strain is induced with a piezoelectric element.

4. A method according to claim 1, wherein the article is fixtured so as to be cantilevered from a fixture.

5. A method according to claim 1, wherein the oscillating force is applied in a direction normal to a surface of the article, the defect being located beneath and in a plane parallel to the surface of the article.

6. A method according to claim 1, wherein the oscillating force is applied in a direction parallel to a surface of the article, the defect being located beneath and in a plane normal to the surface of the article.

7. A method according to claim 1, wherein the article is a ceramic matrix article comprising laminations parallel to a surface of the article.

8. A method of nondestructively detecting defects in an article, the method comprising the steps of:
   vibrating the entire article to induce an oscillating strain in the article; and then
   infrared imaging the article to detect a temperature rise in the article associated with friction caused by the oscillating strain and localized at a defect in the article;

wherein the article is an assembly comprising a first article secured to a second article with a fastener that provides a clamping load to clamp surfaces of the first and second articles together, and the defect is at an interface between the surfaces of the first and second articles as a result of the clamping load being sufficiently low to allow the oscillating strain to cause the frictional heating at the interface.

9. A method according to claim 8, further comprising the step of increasing the clamping load of the fastener after the vibrating and infrared imaging steps.

10. A method of nondestructively detecting defects in an article, the method comprising the steps of:
vibrating the entire article to induce an oscillating strain in the article; and then
infrared imaging the article to detect a temperature rise in the article associated with friction caused by the oscillating strain and localized at a defect in the article;
wherein the article is an assembly comprising a composite article secured to a second article with a fastener that provides a clamping load that clamps a surface of the composite article to a surface of the second article, and the vibrating step causes projecting features on the surface of the composite article to be reduced, the method further comprising the step of increasing the clamping load of the fastener after the vibrating and infrared imaging steps.

11. A method of assembling and nondestructively detecting an assembly defect in an assembly comprising a ceramic matrix composite article secured to a second article with a fastener that provides a clamping load that clamps a surface of the composite article to a surface of the second article, the method comprising the steps of:
fixturing the assembly so as to be secured at at least one nodal point of the assembly;
applying an oscillating force to the assembly at an anti-nodal point of the assembly and in a direction relative to the surfaces of the composite and second articles, the oscillating force inducing an oscillating strain in the composite article that is within the elastic strain region for the composite article, the oscillating strain creating localized friction at an interface of the surfaces of the composite and second articles to cause localized heating of the assembly in the vicinity of the interface; and then
detecting a temperature rise in the vicinity of the interface associated with the localized heating at the interface.

12. A method according to claim 11, wherein the temperature rise is detected with infrared detection means.

13. A method according to claim 11, wherein the oscillating force is applied with a piezoelectric element.

14. A method according to claim 11, wherein the oscillating force is applied in a direction normal to the surfaces of the composite and second articles.

15. A method according to claim 11, further comprising the step of increasing the clamping load of the fastener after the applying and detecting steps.

16. A method according to claim 11, wherein the applying step causes projecting features on the surface of the composite article to be reduced, the method further comprising the step of increasing the clamping load of the fastener after the applying and detecting steps.

17. A method according to claim 11, wherein the assembly is a component of a gas turbine engine.

18. A method according to claim 11, wherein the detecting step comprises displaying a visual image from which the temperature rise in the vicinity of the interface can be seen.

19. A system for nondestructively detecting flaws in an article, the system comprising:

means for fixturing the article to secure at least one nodal point of the article;
means for inducing an oscillating strain in the entire article by applying an oscillating force at an anti-nodal point of the article; and
means for infrared imaging the article to detect a temperature rise in the article associated with friction caused by the oscillating strain and localized at a flaw in the article.

20. A system according to claim 19, wherein the inducing means is operable and controlled so that the oscillating strain is within the elastic strain region for the article.

21. A system according to claim 19, wherein the inducing means comprises a piezoelectric element.

22. A system according to claim 19, wherein the inducing means is operable to induce the oscillating strain by applying an oscillating force in a direction normal to a surface of the article.

23. A system according to claim 19, wherein to inducing means is operable to induce the oscillating strain by applying an oscillating force in a direction parallel to a surface of the article.

24. A system according to claim 19, wherein the article is cantilevered from the fixturing means.

25. A system according to claim 19, wherein the inducing means is operable to apply the oscillating force in a direction normal to a surface of the article, to flaw being located beneath and in a plane parallel to the surface of the article.

26. A system according to claim 19, wherein the inducing means is operable to apply the oscillating force in a direction parallel to a surface of the article, the flaw being located beneath and in a plane normal to the surface of the article.

27. A system for nondestructively detecting an assembly defect in an assembly comprising a ceramic matrix composite article secured to a second article with a fastener that provides a clamping load that clamps a surface of the composite article to a surface of the second article, the system comprising:
means for fixturing the assembly to be secured at at least one nodal point of the assembly;
means for applying an oscillating force to the assembly at an anti-nodal point of the assembly, in a direction relative to the surfaces of the composite and second articles, and which is sufficient to induce an oscillating strain in the composite article that is within the elastic strain region for the composite article and creates sufficient localized friction at an interface of the surfaces of the composite and second articles to cause localized heating of the assembly in the vicinity of the interface; and
means for detecting a temperature rise in the vicinity of the interface associated with the localized heating at the interface.

28. A system according to claim 27, wherein the examining means comprises an infrared detector.

29. A system according to claim 27, wherein the applying means comprises a piezoelectric element.

30. A system according to claim 27, wherein the applying means is operable to apply the oscillating force in a direction normal to the surfaces of the composite and second articles.

31. A system according to claim 27, further comprising means for increasing the clamping load of the fastener.

32. A system according to claim 27, wherein the examining means comprises means for displaying a visual image from which the temperature rise in the vicinity of the flaw can be seen.

* * * * *